(12) United States Patent
Mosley et al.

(10) Patent No.: US 6,653,842 B2
(45) Date of Patent: Nov. 25, 2003

(54) GALVANIC PROBES AS PH AND OXIDATION REDUCTION POTENTIAL SENSORS, CONTROL DEVICES EMPLOYING SUCH PROBES, AND RELATED METHODS

(75) Inventors: Michael David Mosley, Calverton Park, MO (US); Paul Decker, Creve Coeur, MO (US); Thomas Lee Martzall, St. Charles, MO (US)

(73) Assignee: Digital Concepts of Missouri, Earth City, MO (US)

( * ) Notice: Subject to any disclaimer, the term of this patent is extended or adjusted under 35 U.S.C. 154(b) by 0 days.

(21) Appl. No.: 09/901,807

(22) Filed: Jul. 10, 2001

(65) Prior Publication Data

US 2003/0112012 A1 Jun. 19, 2003

(51) Int. Cl.[7] ............... G01N 27/02; G01N 27/416; G01N 27/26; G01F 1/64
(52) U.S. Cl. ............... 324/446; 324/438; 204/400; 204/433; 205/775; 205/787.5
(58) Field of Search ............... 324/446, 438, 324/437; 700/267; 204/412, 416, 196.25, 228.6, 229.1, 196.24, 433, 400; 73/86; 320/134, 136; 205/775, 787.5

(56) References Cited

U.S. PATENT DOCUMENTS

| | | | |
|---|---|---|---|
| 1,089,030 A | 3/1914 | Angell | |
| 3,258,682 A | 6/1966 | Maurer | |
| 3,298,944 A | 1/1967 | Luck | |
| 3,438,871 A | 4/1969 | Minichelli et al. | |
| 3,682,160 A | * 8/1972 | Murata | 600/302 |
| 3,956,094 A | * 5/1976 | Capuano | 204/402 |
| 4,338,175 A | 7/1982 | Binder et al. | |
| 4,506,226 A | * 3/1985 | Luce et al. | 324/459 |
| 4,551,209 A | 11/1985 | Lauks | |
| 5,110,441 A | * 5/1992 | Kinlen et al. | 204/418 |
| 5,146,169 A | * 9/1992 | Morishita et al. | 324/438 |
| 5,218,304 A | * 6/1993 | Kinlen et al. | 324/438 |
| 5,688,385 A | * 11/1997 | Rhees et al. | 204/237 |
| 5,798,940 A | * 8/1998 | Bratton et al. | 700/267 |
| 5,944,635 A | 8/1999 | Butler, Jr. | |
| 6,021,664 A | * 2/2000 | Granato et al. | 73/53.01 |
| 6,115,629 A | 9/2000 | Richter | |
| 6,130,004 A | 10/2000 | Li et al. | |
| 6,202,471 B1 | 3/2001 | Yadav et al. | |

* cited by examiner

Primary Examiner—Anjan K. Deb
(74) Attorney, Agent, or Firm—Thompson Coburn LLP

(57) ABSTRACT

A galvanic probe comprises a sensor electrode and a reference electrode. The sensor electrode has an exposed surface that comprises a noble metal or antimony or bismuth, and, optionally, an oxide or hydroxide thereof. The reference electrode is spaced apart from the sensor electrode and has an exposed surface that comprises zinc or magnesium, and, optionally, an oxide or hydroxide thereof. The probe may be incorporated into a device for controlling the pH and/or ORP of a fluid in a vessel to a desired pH and/or ORP level, incorporated into methods for measuring the pH and/or ORP of a fluid, or used as a galvanic cell.

83 Claims, 8 Drawing Sheets

GALVANIC PROBES AS PH AND OXIDATION REDUCTION POTENTIAL SENSORS, CONTROL DEVICES EMPLOYING SUCH PROBES, AND RELATED METHODS

BACKGROUND OF THE INVENTION (1) Field of the invention

The present invention relates to galvanic probes and cells, and more particularly to the use of such probes and cells in the measurement of various characteristics, such as pH and oxidation reduction potential, of fluids such as water.

(2) Description of the Related Art

It is often necessary or desirable to measure the pH or oxidation reduction potential (ORP) of a fluid. The ORP measures the relative tendency of materials in the fluid to undergo oxidation or reduction (particularly the ability of the fluid to destroy bacteria in it). Moreover, it is often desirable to monitor pH and/or ORP at frequent intervals—or even continuously. Measurement of pH and ORP levels are of interest in a wide variety of industrial, commercial and domestic processes and situations. For example, many chemical processes are pH-dependent or ORP-dependent. The pH or ORP of effluents from factories is commonly of environmental concern. The pH or ORP of water is critical in many settings. A setting familiar to many laypersons is in various water storage systems, such as air conditioning systems or swimming pools. Therefore, for ease of explanation, much of the following discussion will be with reference to the swimming pool setting, although it should be borne in mind that the discussion is likewise applicable to any other situation in which the pH and/or ORP of a fluid is of interest.

In a swimming pool, the quality of the water is closely related to the pH and ORP of the water. In swimming pools, the ORP of the water is a measure of the free chlorine level in the water, which is related to the biological antiseptic quality of the water. Therefore, the pH and chlorine levels of swimming pool water must be monitored to ensure that an adequate quality level is maintained. Conventionally, this is carried out by hand and the owner or other caretaker in charge of maintaining the pool must repeatedly go to the pool with vials and chemicals, scoop out the water into the vials, shake the vials, compare the colors of the resulting solutions to those on charts coordinated with the pool volume to determine the amounts of chemicals to add to restore the proper pH and/or chlorine level, obtain those chemicals, measure them out and add them to the pool. Not only is this a cumbersome process, but if it is not carried out at frequent enough intervals, the quality of the pool water can become unacceptable very quickly. Thus, for example, if the pool caretaker is away for a several days, he or she may return to find a pool filled with murky water. Or the pH or chlorine level may fall out of acceptable range too soon before the next testing and the water may become unhealthful, and the pool caretaker may not realize that fact until it is too late. Therefore, it is desirable to have a pH monitor and/or an ORP monitor that would carry out the measurement task automatically and frequently even continuously—on a real time basis.

Unfortunately, however, current technology is ill equipped for such frequent or continuous monitoring. Conventional pH meters typically comprise a porous glass membrane enclosing a quantity of a liquid about a sensing electrode. For example, commercial pH electrodes typically employ a pair of silver/silver chloride electrodes, one in a saturated potassium chloride solution, the other in hydrochloric acid, encased separately in porous glass, and the pH is determined once the migration of hydrogen ions across the glass membrane has reached equilibrium. Reaching equilibrium can require a substantial amount of time. In fact, if the pH of the fluid being tested changes frequently, such electrodes might never reach equilibrium and so pH measurement may be impossible without extraction of a sample and testing the sample, in which case the measurement is merely historical.

Generally, such commercial pH meters suffer from several other serious drawbacks as well. They are expensive (typically about US$250), unavailable in large quantities, require soaker caps to keep the tips wet when not in use, are affected substantially by temperature, require frequent recalibration, experience substantial signal drift and, as with all electrodes that employ liquid fill solutions, must be maintained in an almost vertical position to keep the electrodes in the tested fluid. Moreover, because the glass and fill solutions required for such electrodes, they are fragile, have limited lives, are incompatible with some industrial processes, especially those in harsh environments.

Other pH meters have been noted in the scientific literature, but are likewise undesirable. Ion selective field effect transistors (ISFETs), in which the signal is based on a selective membrane attached to the gate, have been used, but they also are expensive (about US$300), are unavailable in large quantities (particularly for commercial applications) and are highly sensitive to ambient temperature. Potentiometric solid state sensors, in which measurement is based on ion specific voltage developed between a reference electrode and a measuring sensor, have been described in scientific publications, but their commercialization is extremely limited, and no large-scale production process has been developed. In any event, they also suffer from other serious disadvantages. They require frequent calibration, they suffer from significant drift, they have very limited lives, have limited applicability because some common salts damage their sensor membranes, are expensive (although at about US$20, are less expensive than the previously mentioned meters), are affected substantially by temperature, and while they can be stored dry, they require about 24 hours for stabilization.

Antimony electrodes also have been employed in some pH sensors, usually in combination with a silver/silver chloride reference electrode and glass-encased fill solution, with all the attendant disadvantages of glass membranes and fill solutions noted above. U.S. Pat. No. 5,497,091 describes a pH sensor that employs an antimony electrode in combination with a ceramic reference electrode, but provides no clear description of the ceramic reference electrode. However, known antimony-based pH sensors typically employ a polished antimony surface for enhanced sensitivity and so suffer from deteriorating sensitivity as they lose polish. In addition, known antimony based pH sensors typically also suffer from substantial drift as the quality of the polish diminishes over time, and, as with the other pH sensors dependent on ion exchange between the fluid being tested and the fill solutions, known antimony-based pH sensors frequent recalibration and limited lifetimes due to gradual dilution of the fill solution. Moreover, because they employ a liquid fill solution, they must be maintained in a vertical position. Thus, state of the art pH monitors are unsuitable for many uses, especially those in which a durable, inexpensive and readily available (or easy to manufacture) probe for frequent, accurate, real time pH measurements with low drift.

Monitors for measuring ORP also are available commercially. Their measurements are based on a voltage developed between a silver/silver chloride reference wire in an internal fill solution and a platinum wire isolated from the fill solution. Such monitors also suffer from serious drawbacks, including high cost (about US$250), unavailability in large quantities, limited life based on the fill solution, lengthy response time, the requirement of a soaker cap to keep the tip wet when not in use, and the requirement of all electrodes that employ fill solutions that that they be maintained in an almost vertical position to keep the electrodes in the tested fluid. Thus, as with the state of the art pH monitors, state of the art ORP probes are unsuitable for many uses, especially those in which a durable, inexpensive and readily available (or easy to manufacture) probe for frequent, accurate, real time ORP measurements with low signal drift.

SUMMARY OF THE INVENTION

Briefly, therefore, the present invention is directed to a novel galvanic probe. The probe comprises a sensor electrode and a reference electrode. The sensor electrode has an exposed surface that comprises a noble metal or antimony or bismuth, and, optionally, an oxide or hydroxide thereof. The reference electrode is spaced apart from the sensor electrode and has an exposed surface that comprises zinc or magnesium, and, optionally, an oxide or hydroxide thereof.

The present invention also is directed to a novel device for controlling the pH and/or ORP of a fluid in a vessel to a desired pH and/or ORP level. The device comprises a sensor electrode, a reference electrode, and a circuit arranged such that the electrodes generate a signal when the electrodes are in contact with a fluid such that the electrodes are in electrochemical communication with each other, and wherein the signal is input to and processed by said circuit. If the pH is controlled, the sensor electrode has an exposed surface that comprises antimony or bismuth, and, optionally, an oxide or hydroxide thereof. If the ORP is controlled, the sensor electrode has an exposed surface that comprises a noble metal such as platinum and, optionally, an oxide or hydroxide thereof. The reference electrode is spaced apart from the sensor electrode and has an exposed surface that comprises zinc or magnesium, and, optionally, an oxide or hydroxide thereof.

The present invention also is directed to a novel method for measuring the pH and/or ORP of a fluid. According to the method, electrodes of a probe such as described above are placed into a fluid and the pH and/or ORP is read from the display.

The present invention also is directed to a novel galvanic cell comprising an electrolyte in contact with a sensor electrode having an exposed surface comprising a noble metal or antimony or bismuth, and, optionally, an oxide or hydroxide thereof, and a reference electrode spaced apart from the sensor electrode and having an exposed surface comprising zinc or magnesium and, optionally, an oxide or hydroxide thereof.

Among the several advantages found to be achieved by the present invention, therefore, may be noted the provision of a novel pH and/or ORP probe that is durable, inexpensive available probe for frequent, accurate, real time pH and/or measurements with low drift; the provision of such probe that is less sensitive to temperature variations than are conventional probes; the provision of a novel device for controlling the pH and/or ORP of a fluid in a vessel, such as (but not limited to) water in a swimming pool, to desired pH and/or ORP levels; the provision of a novel device for controlling the pH and/or ORP of a fluid in a vessel, such as (but not limited to) water in a swimming pool, to desired pH and/or ORP levels, including a mechanism for adjusting the pH and/or ORP automatically; and the provision of a novel galvanic cell.

While the principal advantages and features of the present have been described above, a more complete and thorough understanding and appreciation of the invention may be attained by referring to the drawing figures and description of the preferred embodiments, which follow.

BRIEF DESCRIPTION OF THE DRAWINGS

FIG. 5($b$) is a schematic representation of the third embodiment of a probe of the invention wherein both the pH level and ORP level of the fluid are sensed;

Figure 1:
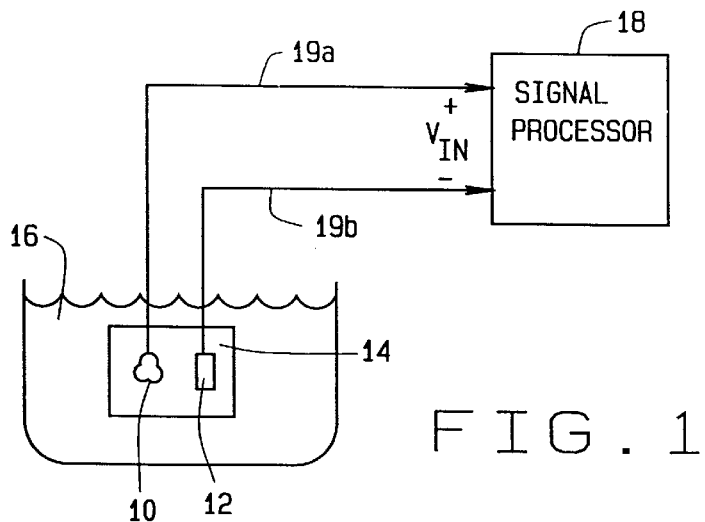
FIG. 1 is a schematic representation of a first embodiment of a probe of the present invention.

Reference characters in these Figures correspond to reference figures in the following detailed description of the preferred embodiments.

DETAILED DESCRIPTION OF THE PREFERRED EMBODIMENTS

In accordance with the present invention, it has been discovered that, surprisingly, certain combinations of electrode materials can be used to construct extremely low cost, but long life and highly durable galvanic probes that can be used to produce sensors that give highly accurate and quick measurements of certain characteristics, such as pH and oxidation reduction potential (ORP), of the electrolytic fluids in which they are placed, while eliminating the need for delicate and fragile porous glass and internal fill solutions. The sensors produce highly repeatable and very stable signals and so often require only a single, simple initial calibration. The signal has been found to be generally independent of the sizes of the electrodes and the distance between them, and that are substantially less affected by temperature compared to prior art sensors. The signals are directly proportional to pH or ORP, as the case may be, are high repeatable, and require only a simple initial calibration. In fact, the sensors are stable enough to allow for frequent measurements and have such low drift that they have been found to be capable of providing frequent, perhaps even continuous, real time measurements of such fluid characteristics with probe materials costing well under US$1. The probe does not require either fill solutions or glass materials. Rather it may be constructed of extremely durable materials that not only can withstand rough treatment, but also can be used in a wide variety of systems, including harsh environments. The probe is not dependent on vertical or any other position orientation and can be stored dry with a minimum of stabilization time as compared to prior art sensors. Moreover, because the probe of this invention employs electrode materials that are galvanic. In fact, because they generate a current upon contact with an electrolyte, the probe may be used to produce a galvanic cell.

The galvanic probe of this invention comprises at least one sensor electrode in combination with a reference electrode. In particular, it has been found that an antimony or bismuth sensor electrode may be used in combination with a zinc or magnesium reference electrode in the presence of an electrolytic fluid to produce a signal in the form of a current having a voltage differential (a potential difference between the electrodes) directly proportional to the pH of the fluid in the manner to be discussed in more detail below. Assuming constant resistance, therefore, the amperage of the current is likewise directly proportional to the pH of the fluid. Similarly, it has been found that a noble metal sensor electrode may be used in combination with a zinc or magnesium reference electrode in the presence of an electrolytic fluid to produce a signal in the form of a current having a voltage differential potential difference between the electrodes)—and so also an amperage—directly proportional to the ORP of the fluid in the manner also to be discussed in more detail below. The antimony or bismuth electrode and the noble metal electrode are referred to herein as "sensor" electrodes in distinction to the reference electrode. The electrolyte fluid may be any nonmetallic fluid, particularly a liquid, that is a conductor in which electric current is carried by movement of ions in the fluid. As used herein, the term "conductor" refers to electrical conductors.

It is envisioned that the probe of the present invention would be used typically in aqueous electrolytic liquids. Among such liquids may be noted water itself and aqueous electrolytic solutions. An electrolytic fluid of particular interest is swimming pool water and some of the following discussion will be directed specifically thereto. However, this discussion should not be viewed as limiting, as the probe of the present invention has wide-ranging applications, from measurements of pH and ORP in fluids in chemical and industrial syntheses, processes and effluents, to such measurements in streams and lakes. In fact, it is contemplated that the probes of the present invention can be used to produce sensors that may be may be used in any system containing an electrolytic fluid in which it is desired to measure pH or ORP.

With respect to the antimony or bismuth electrode, antimony is preferred over bismuth and so the following discussion will refer to antimony. However, it should be understood that the same description is applicable to bismuth as well. Thus, the antimony or bismuth electrode will hereinafter be referred to as "the antimony electrode," although it will be recognized that, except as noted, the same explanation will apply for a bismuth electrode, but with reference to bismuth instead of antimony.

Although in the most preferred embodiment, it is expected that the entire antimony electrode will be a piece of solid antimony material, it is only necessary that at least part of an exposed surface of the antimony electrode be antimony. As used herein, an "exposed surface" of an electrode means a surface of the electrode that comes into direct contact with an electrolytic fluid when the electrode is placed into the fluid. Thus, other than a solid piece of antimony, examples of the antimony electrode wherein at least part of an exposed surface of the electrode is antimony include a substrate coated with antimony, a substrate with a portion of its surface coated with antimony, and so forth. Of course, if a part of the exposed surface of the electrode is a material other than antimony, it is preferred that the material other than antimony be inert in the sense that it does not interfere with the subject electrolytic reaction occurring with the antimony; that is, perhaps: $2Sb+3H_2O \leftrightarrows Sb_2O_3+6H^++6e^-$ ($2Bi+3H_2O \leftrightarrows Bi_2O_3+6H^++6e^-$ for bismuth).

The antimony need not be polished as in certain prior art pH sensors that employ antimony electrodes. Thus, efficacy of the antimony electrode has not been found to degrade upon use, despite the formation of antimony oxide (also called antimony trioxide—with respect to bismuth, bismuth trioxide or bismuth tetroxide) or possibly even antimony hydroxide resulting from use in the probe of this invention. Thus, it is contemplated that the exposed surfaces of the antimony electrode may also bear such oxides or hydroxides, particularly once used.

Similarly to the antimony electrode, at least part of an exposed surface of the noble metal electrode is a noble metal. Preferably, the noble metal is platinum, gold or silver, most preferably platinum. Thus, the noble metal electrode may be any solid electrode wherein at least part of an exposed surface of the electrode is a noble metal. Preferably, the electrode is a solid piece of the noble metal, but it need not be. For example, other than a solid piece of the noble metal, the noble metal electrode may be a substrate coated with the noble metal, a substrate with a portion of its surface coated with the noble metal, and so forth. Of course, if a part of the exposed surface of the electrode is a material other than the noble metal, it is preferred that the material other than the noble metal be inert in the sense that it does not interfere with the subject electrolytic reaction with the noble metal; that is, for example, in the case of platinum, perhaps:

$$Pt+H_2O \leftrightarrows PtOH+H^++e^-$$

$$PtOH \leftrightarrows HOPt \text{ (rearrangement)}$$

$$HOPt \leftrightarrows Opt+H^++e^-$$

Also as with the antimony electrode, the platinum need not be polished. Thus, efficacy of the noble metal electrode has not been found to degrade upon use, despite the formation of oxides or hydroxides of the noble metal resulting from use in the probe of this invention. Thus, it is contemplated that the exposed surfaces of the noble metal electrode may also bear such oxides or hydroxides, particularly once used.

At least part of an exposed surface of the reference electrode is zinc or magnesium. Although the reference electrode may be either zinc or magnesium, the present inventors have found less drift in readings when the reference electrode is zinc than when it is magnesium, and so zinc is preferred. The reference electrode may be any solid electrode wherein at least part of an exposed surface of the electrode is zinc or magnesium. Preferably, the electrode is a solid piece of zinc or magnesium, but it need not be. For example, the reference electrode may be a solid piece of zinc or magnesium, a substrate coated with zinc or magnesium (e.g., galvanized sheet metal), a substrate with a portion of its surface coated with zinc or magnesium, and so forth. Of course, if a part of the exposed surface of the electrode is a material other than zinc or magnesium, it is preferred that the material other than zinc or magnesium be inert in the sense that it does not interfere with the subject electrolytic reaction with the zinc or magnesium; that is, for example: $ZnO+2H^++2e^- \leftrightarrows Zn+H_2O$ or $MgO+2H^++2e^- \leftrightarrows Mg+H_2O$. However, it has been found that the efficacy of the electrode is greatly—and deleteriously—affected by the presence of other impurities, such as trace amounts of tin, lead and copper. This is typically not a problem with most fluids, including tap water such as may be found in pools and spas and the like. However, the deleterious impurities need not arise from the fluid itself. They might also derive from the electrodes. In fact, it has been found that the sensitivity of the probe of the present invention decreases significantly if the reference electrode incorporates zinc of lower purity than about 99.99%, and especially lower than about 99.9%, is greatly preferred. Accordingly, it is preferred that the reference electrode comprise zinc of purity at least about 99.9%, especially at least about 99.99%.

When discussing purity, it will be appreciated that the electrolytic process may cause the materials of the electrodes to oxidize and so some of the material may be present in oxidized form. As with the sensor electrodes, efficacy of the reference electrode has not been found to degrade upon use, despite the formation of oxides or hydroxides of the zinc or magnesium resulting from use in the probe of this invention and the zinc or magnesium need not be polished and it is contemplated that the exposed surfaces of the reference electrode may also bear such oxides or hydroxides, particularly once used. In fact, the electrolytic process results in increases and decreases in the proportion of the reference electrode that is in the reduced state versus oxidized state (and inversely corresponding increases and decreases in the proportion of the sensor electrode(s) that in the reduced state versus oxidized state) as the pH or ORP level changes. In the context of the present application, therefore, the fact that some of the material may be in oxidized form is not viewed as indicating a lower the purity of the material. Thus, in calculating purity values, the oxidized form of the material should be considered as part of the pure material component and associated anions, e.g., oxide or hydroxide, should be discounted.

In general, the quality of the signal produced by the electrodes when in operation in a galvanic probe of this invention is independent of the sizes and shapes of the electrodes, at least within the reasonable limits of typical electrode sizes. However, by way of illustration, it has been found that a practical size for a flat, rectangular zinc reference electrode is at least about 0.25 inches wide×0.375 inches long×0.031 inches thick, and for a flat, round zinc reference electrode is at least about 0.375 inches in diameter×0.125 inches thick. Platinum sensor electrodes in the form of a wire 0.005 inches thick×0.5 inches long have been found to yield high quality results as well.

A probe of this invention comprises one or both types of the sensor electrodes described above in combination with the reference electrode described above. Although both types of sensor electrodes may be used at the same time with a single reference electrode or with a separate reference electrode designated for each type of sensor electrode, there is generally no advantage to use of separate reference electrodes, particularly when measurements associated with both types of sensor electrodes are to be taken in proximity to each other. Thus, although references herein to "the" or "a" reference electrode in the systems employing both types of sensor electrodes are intended to encompass situations wherein a plurality of reference electrodes are employed, a probe with a single reference electrode is the preferred embodiment.

The probe is a galvanic probe, and may be used as a galvanic cell as well as a probe. Thus, when the electrodes of a probe of this invention are an electrolytic fluid is contacted with the probe such that the sensor electrode(s) and reference electrode of the probe are in electrochemical communication and the reference electrode and sensor electrode(s) are further interconnected with an electric circuit, a current of electricity is generated and flows through the circuit from the reference electrode to the sensor electrode. By "electrochemical communication," what is meant is that the electrolytic fluid is in contact with both the sensor electrode(s) and the reference electrode such that ions may move therebetween.

In an especially desirable form, the electrodes are mounted on a substrate. This not only provides a convenient way to handle and to use the electrodes as a single unit, but also maintains the distance(s) between the electrodes. The electrodes, of course, should be spaced apart from one another (measurements of the characteristics of the fluid are dependent on the employment of the fluid as an electrolyte between the electrodes), but the electrodes need not be far apart. In fact, it is preferred that the sensor electrode (or each sensor electrode if more than one is employed) be relatively close to the reference electrode—say, as close as 1 mm—to avoid significant fluid flow between the electrodes continually changing or deleteriously affecting the measurements.

The substrate may be any other material that does not interfere with the electrolytic process. Thus, the substrate should not be or comprise, for example, a conductor, such as metal, or an ionic compound soluble in the electrolytic fluid (of course the substrate should be insoluble in the fluid, even if nonionic), but may be plastic (e.g., acrylic), ceramic, wood, and so forth. Preferably, the substrate is solid and sturdy. The electrodes may be affixed to the substrate in any manner, including gluing, cementing, friction-fitting, not metallic banding, etc. Of course, preferably the material used in affixing the electrodes to the substrate likewise is not of the type that interferes with the electrolytic process.

The probe may comprise the reference electrode and the antimony or bismuth sensor electrode, the reference electrode and the noble metal sensor electrode or the reference electrode(s) and both types of sensor electrodes. A probe consisting of the reference electrode and the antimony or bismuth electrode has been found to provide an excellent pH sensor, as will be discussed further below. A probe consisting of the reference electrode and the noble metal electrode has been found to provide an excellent ORP sensor, as will be discussed further below. A probe comprising all three types of electrodes has been found to provide an excellent sensor of both pH and ORP. If the probe includes all three types of electrodes, it is preferred that the reference electrode be a single electrode positioned between the two types of sensor electrodes.

FIG. 1 depicts a preferred embodiment of the invention wherein the probe functions as either a pH sensor or an ORP sensor. The probe comprises a sensor electrode 10 and a reference electrode 12, which may be mounted on a substrate 14 as discussed above. If the sensor electrode 10 is an antimony or bismuth electrode, the probe may be used as a pH sensor. If the sensor electrode 10 is a noble metal electrode, the probe may be used as an ORP sensor.

When the electrodes 10 and 12 are placed in the electrolytic fluid 16, the electrodes initiate electrochemical communication with each other and a voltage differential $V^{IN}$ develops between the sensor electrode 10 and reference electrode 12. Therefore, a galvanic cell is created and when a circuit between the electrodes is completed, the electrodes, in interaction with the fluid, generate a current galvanically and the current flows to and through a circuit from the reference electrode to the sensor electrode. The circuit is represented schematically in FIG. 1 by the signal processor 18 and the conductive inputs 19a and 19b extending between the electrodes and the signal processor 18. The current therefore provides an input to a circuit represented schematically in FIG. 1 as the signal processor 18. The input may be processed by the signal processor 18 with respect to any of the characteristics of that current or information communicated by that current, such as voltage or amperage of the current. For the sake of simplicity, the voltage differential is identified in FIG. 1 as $V_{IN}$, however, any current characteristic or information may be the input processed by signal processor 18 as desired for the particular processing of interest.

Figure 2:
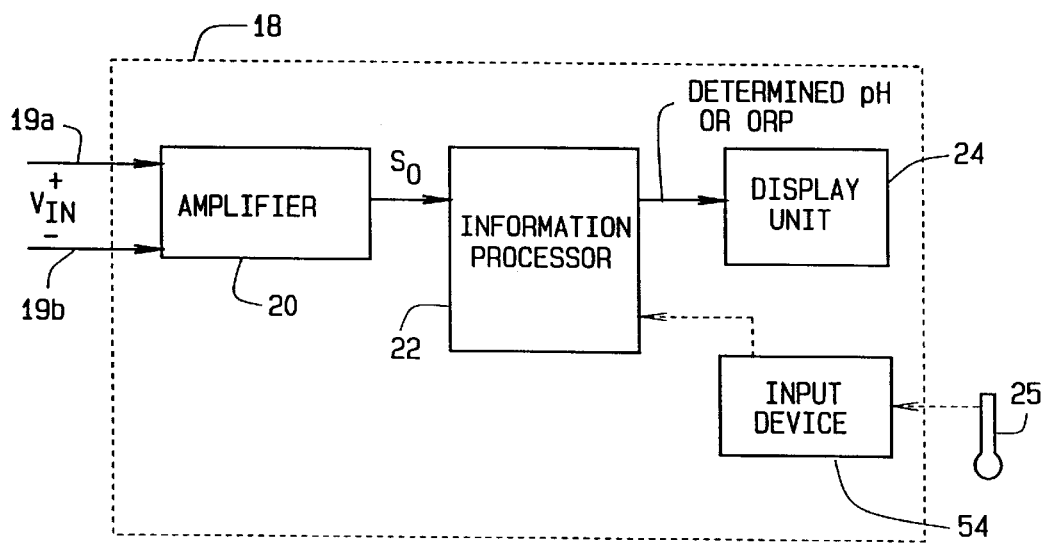
FIG. 2 is a schematic representation of the signal processor shown in FIG. 1.

A more detailed schematic representation of the signal processor 18 is shown in FIG. 2. As illustrated in FIG. 2, the signal processor 18 may comprise an amplifier 20, if so desired. For example, the amplifier may be set to a X1 gain and serve as a buffer or set to, for example, a X9 gain to reduce the input range or to enlarge the output range in an op-amp type circuit to amplify the signal prior to the detection device. If an amplifier 20 is used, the inputs 19a and 19b are directed to the amplifier 20. The output signal $S_O$ of the amplifier 20 then is routed to an information processor 22. If the amplifier 20 is omitted, the inputs 19a and 19b are routed directly to the information processor 22, in that case $S_O$ represents the inputs 19a and 19b.

The information processor 22 may processes the signal $S_O$ in any of a multitude of ways. Thus, the information processor 22 may be but is not necessarily a microprocessor. In fact, the information processor 22 may be any item that is activated by, responds to, operates on or measures some characteristic of an electric current. For example, information processor 22 may be a light bulb, an alarm, a electro-activated switch or any other such devices or combination of devices that operate on an electrical current.

Preferably, however, the information processor 22 is a detection device for detecting a characteristic of the current or information communicated by the current, most preferably in combination with a processor, such as a microprocessor to translate the current or information to another form (a numerical value, a reading on a gauge, a new signal, etc.). In one embodiment, the information processor 22 may be a voltmeter, in which case, the current characteristic would be the voltage differential $V_{IN}$ (which may be expressed, for example, in millivolts) between the electrodes, or an ammeter, in which case the characteristic would be the amperage of the current $I_{IN}$ (which may be expressed, for example in milliamperes). In another embodiment, the information processor measures the voltage or amperage of the current and translates that information to a signal indicative of pH or ORP. Because the current generated by the probe is relatively small, the information processor 22 should have a low impedance. However, in a preferred embodiment, the device detects or measures voltage.

When the probe is a pH sensor, the sensor electrode 10 exchanges hydrogen ions with the fluid 16. This exchange of ions can be measured as the amperage of the current $I_{IN}$ flowing through the circuit or the voltage differential $V_{IN}$ between the electrodes and is reflective of the pH level of the fluid 16. Surprisingly, it has been found that the amperage of the current $I_{IN}$ and the voltage $V_{IN}$ are both linearly related to the pH. In other words, a graph of the current amperage $I_{IN}$ or the voltage $V_{IN}$ versus the pH of the fluid on Cartesian coordinates is a straight line. Thus, the pH may be derived from the current $I_{IN}$ or the voltage $V_{IN}$ may be derived from the simple equations $AI_{IN}+B$ or $AV_{IN}+B$, respectively, wherein A is a constant corresponding to the slope of the line and B is a constant corresponding to the translation (shifting) of the line from the origin.

When the probe is an ORP sensor, the resultant voltage differential $V_{IN}$, which develops as oxidation and reduction occurs in the fluid 16, is reflective of the ORP level of the fluid 16. Similarly, it also has been found, again surprisingly, that the amperage of the current $I_{IN}$ and the voltage $V_{IN}$ are both linearly proportional (subject to translation) to the ORP. In other words, a graph of the amperage of the current $I_{IN}$ or the voltage $V_{IN}$ versus the ORP of the fluid on Cartesian coordinates is a straight line. Thus, the ORP may be derived from the current $I_{IN}$ or the voltage $V_{IN}$ may be derived from the simple equations $AI_{IN}+B$ or $AV_{IN}+B$, respectively, wherein A is a constant corresponding to the slope of the line and B is a constant corresponding to the translation (shifting) of the line from the origin.

In a preferred embodiment in which the probe is a pH or ORP sensor, the basic function of the information processor 22 is to determine from the input signal $S_O$ what the actual pH level or ORP level of the fluid 16 is. The information processor 22 translates the signal $S_O$ to translated information directly indicative of the pH or ORP, respectively, of the fluid contacted by the electrodes according to the noted equations.

Because the voltage differential and amperage are linearly related to the pH and ORP, calibration is simple. A reading indicative of voltage differential or amperage of just two samples of known pH or ORP defines the line expressing the linear relationship and thus determines A and B in the noted equations.

Once the translated information directly indicative of the pH level or ORP level is determined by the information processor 22, such data can be supplied to a display unit 24, which is configured to display the determined pH level or ORP level to a user. Preferably, the display unit can be an LCD interfaced with the information processor 22. However, it is easily understood by one of ordinary skill in the art that the display unit can be virtually any device that can communicate the pH level or ORP level in a meaningful way to a user, including but not limited to a needle and gauge calibrated to translate the information processor output to a pH level of ORP level or an LED display configured to identify the pH/ORP level.

Also, it must be noted that the task of designing the exact circuitry used by the information processor 22 to process the sensed data signal $S_O$ is well within the routine knowledge of one of ordinary skill in the electronic arts following the teachings of the invention. The inventor herein envisions that a vast number of data processing circuits of widely varying complexity can be developed for effectively determining the pH level or ORP level from the sensed data signal $S_O$. For example, as noted above, the data processor 18 can be as simple as a voltmeter connected to the electrode outputs (upon reading the voltage from the voltmeter, a user could consult a chart depicting pH/ORP levels as a function of voltage), or can be as complex as logic array specifically designed to determine the pH/ORP level from the sensed data signal $S_O$.

Figure 3:
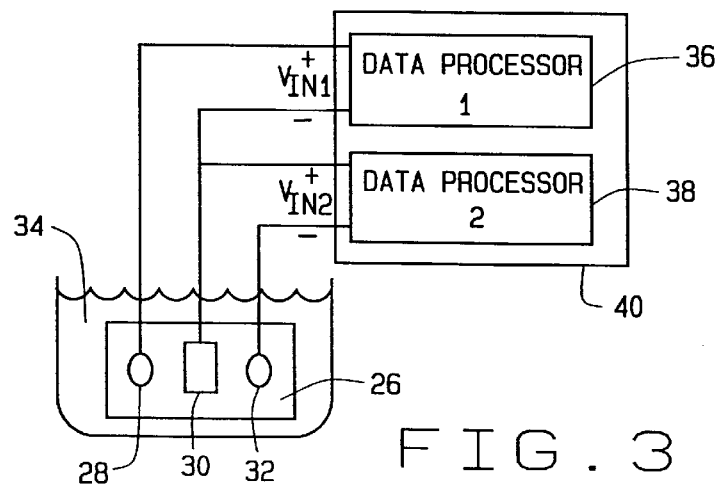
FIG. 3 is a schematic representation of a second embodiment of the present invention wherein the probe functions as both a pH sensor and an ORP sensor.

FIG. 3 depicts a second embodiment of the invention wherein the probe functions as both a pH sensor and an ORP sensor. In this embodiment, the substrate 26 includes three electrodes: a first sensor electrode 28 for sensing the pH level of fluid 34, a reference electrode 30, and a second sensor electrode 32 for the ORP of fluid 34. For simplicity in the following discussion, the first sensor electrode 28 will be denoted as a pH sensor while the second sensor electrode 32 will be denoted as an ORP sensor. Preferably, the reference electrode 30 is positioned between the first and second sensor electrodes 28 and 32.

In this embodiment, the voltage differential $V_{IN1}$ that develops between the first sensor electrode 28 and the reference electrode 30 will be reflective of the pH level of the surrounding fluid 34 and will be supplied to a first data processor 36. The voltage differential $V_{IN2}$ that develops between the second sensor electrode 32 and the reference electrode 30 will be reflective of the ORP level of the surrounding fluid 34 and will be supplied to a second data processor 38. The first and second data processors 36 and 38 can be collectively referred to as data processor 40. The first data processor 36 can be implemented as described above in connection with FIGS. 1 and 2 except that it will be specifically focused on determining the pH level from the data signal $V_{IN1}$. The second data processor 38 can also be implemented as described above in connection with FIGS. 1 and 2 except that it will be specifically focused on determining the ORP level from the data signal $V_{IN2}$. Also, as would be apparent to those of ordinary skill in the art, the tasks of the first and second data processors 36 and 38 can be implemented using the same microprocessor, wherein such a microprocessor is configured to separately receive and process both $V_{IN1}$ and $V_{IN2}$.

Figure 4:
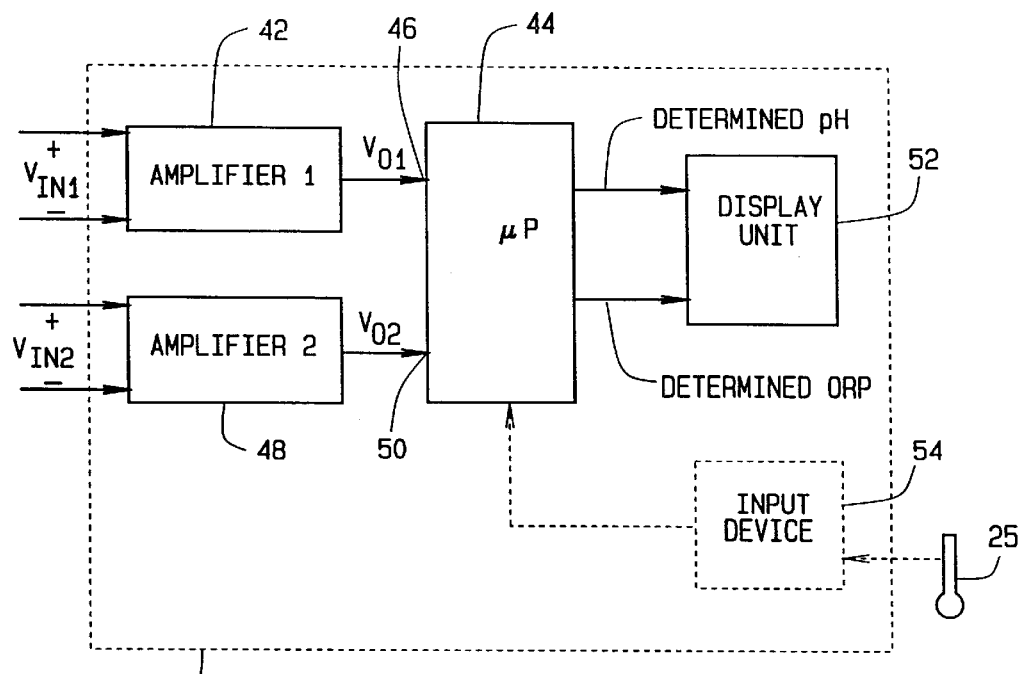
FIG. 4 is a schematic representation of a data processor employed in an embodiment of the probe of the present invention.

FIG. 4 shows a preferred data processor 40 wherein a first amplifier 42 is used to amplify $V_{IN1}$ and a microprocessor 44 receives the amplification of $V_{IN1}$ via a first input 46. A second amplifier 48 is used to amplify $V_{IN2}$, and the microprocessor 44 receives the amplification of $V_{IN2}$ via a second input 50. The microprocessor 44 can be configured to separately process the pH data signal received via first input 46 and the ORP data signal received via second input 50. As discussed above, the microprocessor 44 can be configured in a variety of ways to determine the pH level and ORP level from the sensed data signals. Once the pH and ORP levels are determined, a display unit 52 interfaced with the microprocessor can display those levels.

In more sophisticated versions of the first and second embodiments of the invention, the data processor 18 of FIG. 1 and the data processor 40 of FIG. 4 can be configured to determine from the pH level or ORP level how much of a treatment chemical is needed to alter the pH level or ORP level of the fluid to a suitable value. Thus, instead of or in addition to the translated information indicative of pH and/or ORP as determined by the information processor being directed to a display that displays the pH or ORP, it may be directed to a display indicating the amount of treatment chemical should be added to alter the pH or ORP level, or even to a mechanism for adding such amount, as will be discussed in more detail below.

For example, when the probe is used in connection with swimming pools, the user could quickly learn how much of a chemical must be added to the pool by simply inserting the electrodes in the pool water and reading from the display unit how much treatment chemicals need to be added. Alternatively, the electrodes can remain submerged perpetually in the pool water, providing continuous data, intermittent data or data upon command such as by activating a switch. In the case of a swimming pool, the ORP reading may be desirable in the form of the chlorine level of the water. To implement this design, it is preferable that an input device 54 be interfaced with a microprocessor (which may be the information processor) so that a user can inform the microprocessor of certain information such as the desired pH level and/or chlorine level of the pool water, the volume of the pool being analyzed. This input device can be any known device for inputting data from a keypad to a touch-screen to a voice recognition device. Of course, the pool volume could be prestored in the microprocessor.

The probe of the present invention is substantially less temperature dependent than are some prior art probes and, depending on the application, the probe may be used with or without temperature compensation. If a probe of the present invention is to include compensation for the temperature of the fluid, an additional input may be the temperature of the water of the fluid being tested. Accordingly, a temperature sensing device, such as a thermometer 25, may provide an input of information indicative of the temperature of the fluid. The apparent pH/ORP levels may then be corrected to true pH/ORP levels, for example, by resort to reference tables prepared from tests conducted at various temperatures on fluid samples of known pH/ORP or from mathematical relationships determined from such tests.

Again, for illustrative purposes, attention is directed to swimming pools. Once the microprocessor knows the pH/ORP level of the pool, the volume of the pool and, optionally the temperature of the pool water, the microprocessor can be configured to determine how much treatment chemical is needed to bring the pool back to an acceptable pH/ORP level. For example, a lookup table referencing chemical amounts by pool volume and pH/ORP levels can be stored in microprocessor memory and accessed once the pool volume is entered via input device 54 and the pH/ORP level has been determined. Alternatively, the microprocessor can be configured to calculate the amount of chemical from predetermined formulas.

Figure 5A:
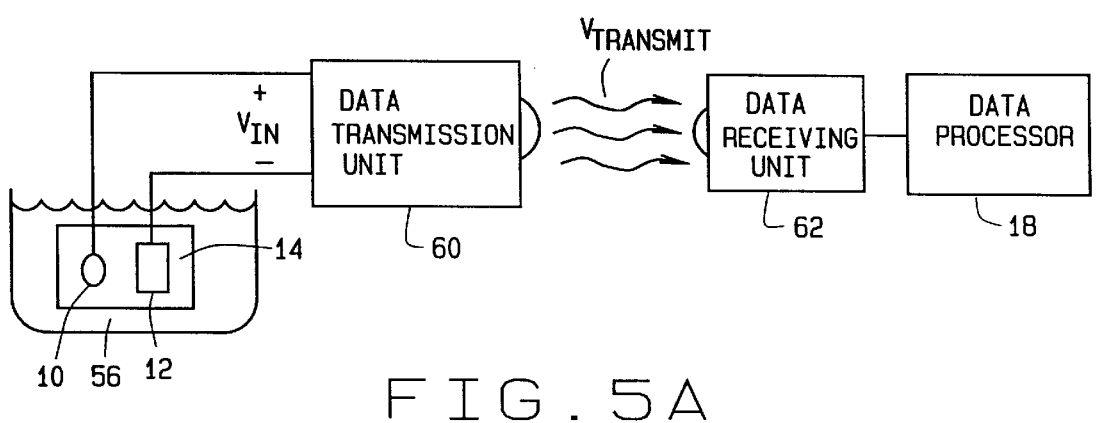
FIG. 5($a$) is a schematic representation of a third embodiment of a probe of the invention wherein either the pH level or ORP level of the fluid is sensed, but not both.
Figure 5B:
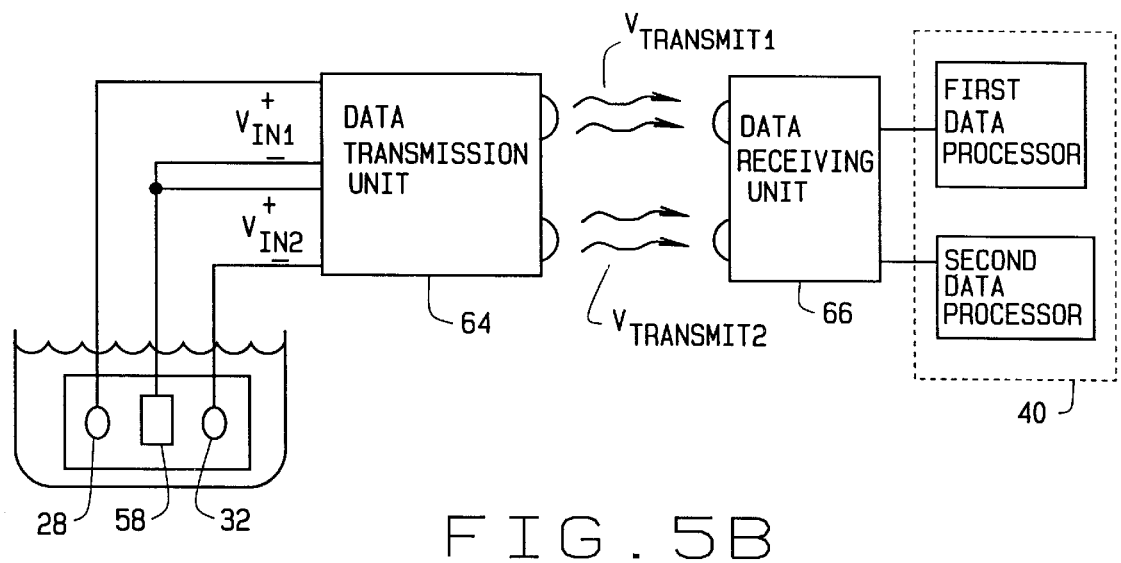

Also, in a third embodiment of the present invention, shown in FIGS. 5(a) and 5(b), the probe can be implemented such that the sensing functions and data processing functions are performed separately from each other. FIG. 5(a) shows the third embodiment of the invention wherein either the pH level or ORP level of the fluid is sensed, but not both (the electrode assembly 56 includes only a single sensor electrode 10). FIG. 5(b) shows the third embodiment of the invention wherein both the pH level and ORP level of the fluid are sensed (the electrode assembly 58 includes both a first sensor electrode 28 and a second sensor electrode 32). In FIG. 5(a) a data transmission unit 60 is interfaced with the electrode assembly 56. The data transmission unit 60 receives the sensed data signal $V_{IN}$, converts $V_{IN}$ to an output signal $V_{TRANSMIT}$, and transmits $V_{TRANSMIT}$ to a remote data receiving unit 62. In FIG. 5(b) a data transmission unit 64 is interfaced with the electrode assembly 58. The data transmission unit 64 receives the sensed data signals $V_{IN1}$ and $V_{IN2}$, converts $V_{IN1}$ and $V_{IN2}$ to output signals $V_{TRANSMIT1}$ and $V_{TRANSMIT2}$, and transmits $V_{TRANSMIT1}$ and $V_{TRANSMIT2}$ to a remote data receiving unit 66. The data receiving units 62 and 66 of FIGS. 5(a) and (b) are then interfaced with data processors 18 and 40 respectively. The data receiving units convert the signal received from the data transmission units to a format appropriate for the data processors 18 and 40. Of course such data transmission can occur at any of a number of points in the information processing process, so that a characteristic of or information from the current from the electrodes can be transmitted, with the bulk of processing carried out at the receiving end, or the bulk of the processing can be carried out prior to transmission.

The data transmission units 60 and 64 can be coupled to the data receiving units 62 and 66 via any known technique of wireless communication between remote locations, for example RF communication, infrared (IR) communication, etc. A wide spectrum of available techniques for transmitting data between spatially separated locations, the exact technique used to transmit the sensed data signal(s) to the remote data processor will be readily apparent to those of ordinary skill in the electronic arts. In one preferred embodiment, the data transmission units may be encased in a small housing (with electrodes exposed) that may be adapted to float freely in a pool.

Figure 6:
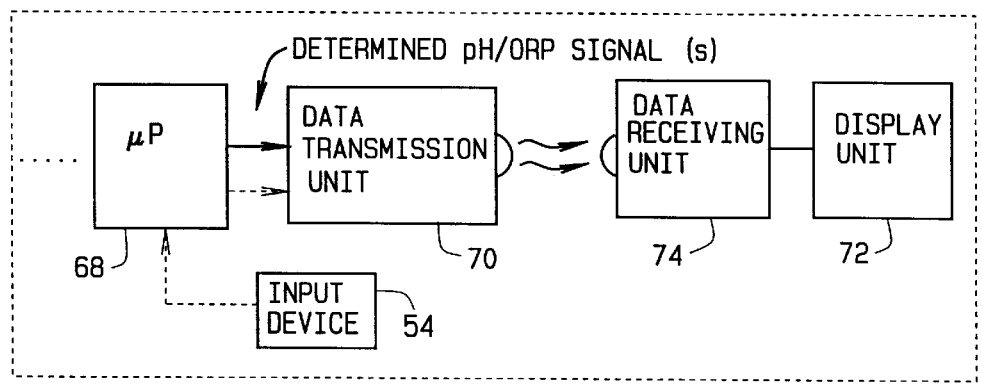
FIG. 6 is a schematic representation of a fourth embodiment of a probe of the present invention wherein the tasks of the data processor are distributed between remote components.

FIG. 6 shows a fourth embodiment of the present invention wherein the tasks of the data processor are distributed between remote components. The output from microprocessor 68 (which can be signal reflective of the pH level, ORP level, or amount of treatment chemical needed) can be interfaced with a data transmission unit 70 as described above. A remote display unit 72 can be interfaced with a data-receiving unit 74 as described above. As explained above, the data transmission unit and data receiving unit can be coupled using any known technique of wireless communication between remote locations.

Figure 7:
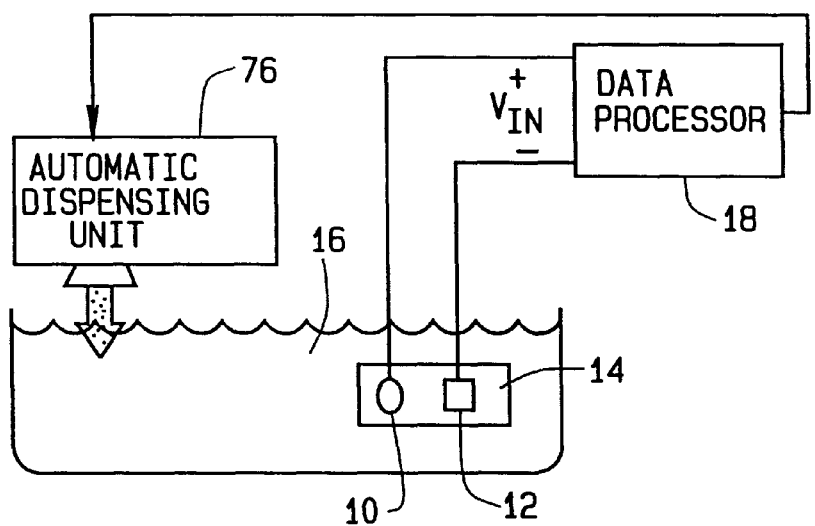
FIG. 7 is a schematic representation of an embodiment of a probe of the present invention wherein only pH or ORP is sensed by the electrodes.
Figure 8:
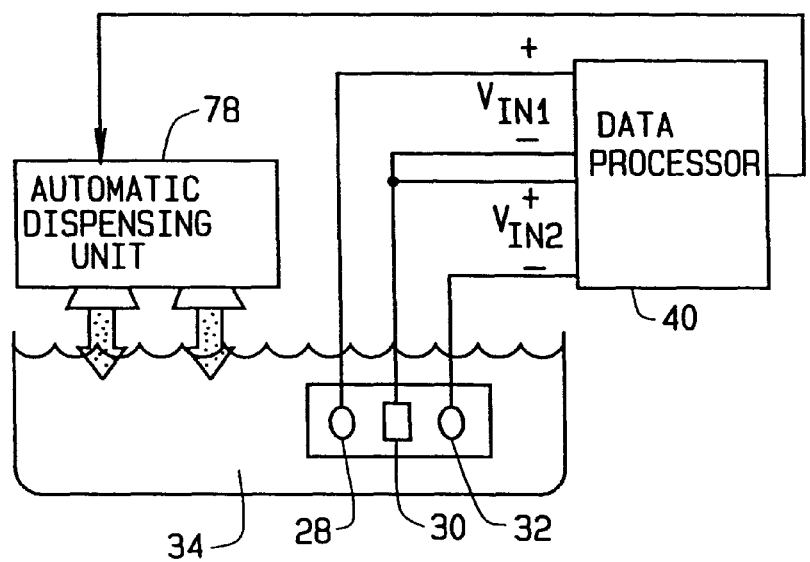
FIG. 8 is a schematic representation of an embodiment of a probe of the present invention, similar to that of FIG. 7, but wherein the electrodes sense both pH and ORP.

FIGS. 7 and 8 depict a fifth embodiment of the invention, wherein chemicals are automatically added to the probed fluid in response to the sensed and measured pH or ORP level. FIG. 7 depicts the invention wherein only pH or ORP is sensed by the electrodes 10 and 12. FIG. 8 depicts the invention wherein both pH and ORP are sensed by the electrodes 28, 30, and 32.

In FIG. 7, an automatic dispensing unit 76 is interfaced with the data processor 18. The automatic dispensing unit will have stored therein a given amount of chemical(s) needed to change either the pH level or ORP level of the fluid 16 to a desired level. In response to instructions from the data processor 18, the automatic dispensing unit will be configured to dispense an appropriate amount of the stored chemical(s) such that the fluid will achieve a desired pH or ORP level. Because the appropriate amount of chemical(s) needed to be added to the fluid 16 will vary as a function of the volume of the fluid 16, the data processor will need data identifying the fluid's volume. As explained above, the data processor 18 may include an input device interfaced to a microprocessor that allows a user to enter the fluid's volume (i.e., the volume of the user's pool). Alternatively, this pool volume can be pre-stored in the microprocessor. The data processor 18 will need to translate the sensed data signal $V_{IN}$, translate that signal to a pH level or ORP level, and then translate the determined pH/ORP level to an amount of chemical(s) that needs to be dispensed into the fluid 16 (this amount will be a function of the fluid's volume). Of course, the data processor 18 can be configured to skip the step of determining the pH/ORP level and translate the data signal $V_{IN}$ directly to an amount of chemical(s) needed to make the appropriate pH or ORP adjustment in the fluid.

In FIG. 8, the configuration of components is very similar to that of FIG. 7 except that both the pH level and ORP level are being sensed, and therefore the automatic dispensing unit will need to be configured to dispense the chemicals needed to make appropriate adjustments to both the pH level and ORP level of the fluid 34. Because the exact design of automatic dispensing units 76 and 78, wherein a measured amount of stored chemical(s) is (are) controllably dispensed in response to an input signal, is well within the common knowledge of a person of ordinary skill in the electronic and mechanical arts, the inventor herein envisions that a wide variety of automatic dispensing units can be developed in accordance with the teachings of this invention, and will leave such routine designs to those ordinarily-skilled artisans.

The data processors 18 and 40 in the embodiments of FIGS. 7 and 8 can also include other devices to convey information relating to the pH/ORP, such as a display unit for displaying the pH/ORP as discussed above and/or an alarm programmed to activate when the pH/ORP moves outside a pre-set range.

It is also contemplated that in some forms, the electrodes may generate enough current to run the data processor, rendering the unit self-powering. Alternatively, the data processor, displays, alarms, dispensers or other may be power by solar energy, batteries or wall current, etc.

The following examples describe preferred embodiments of the invention. Other embodiments with the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Figure 9:
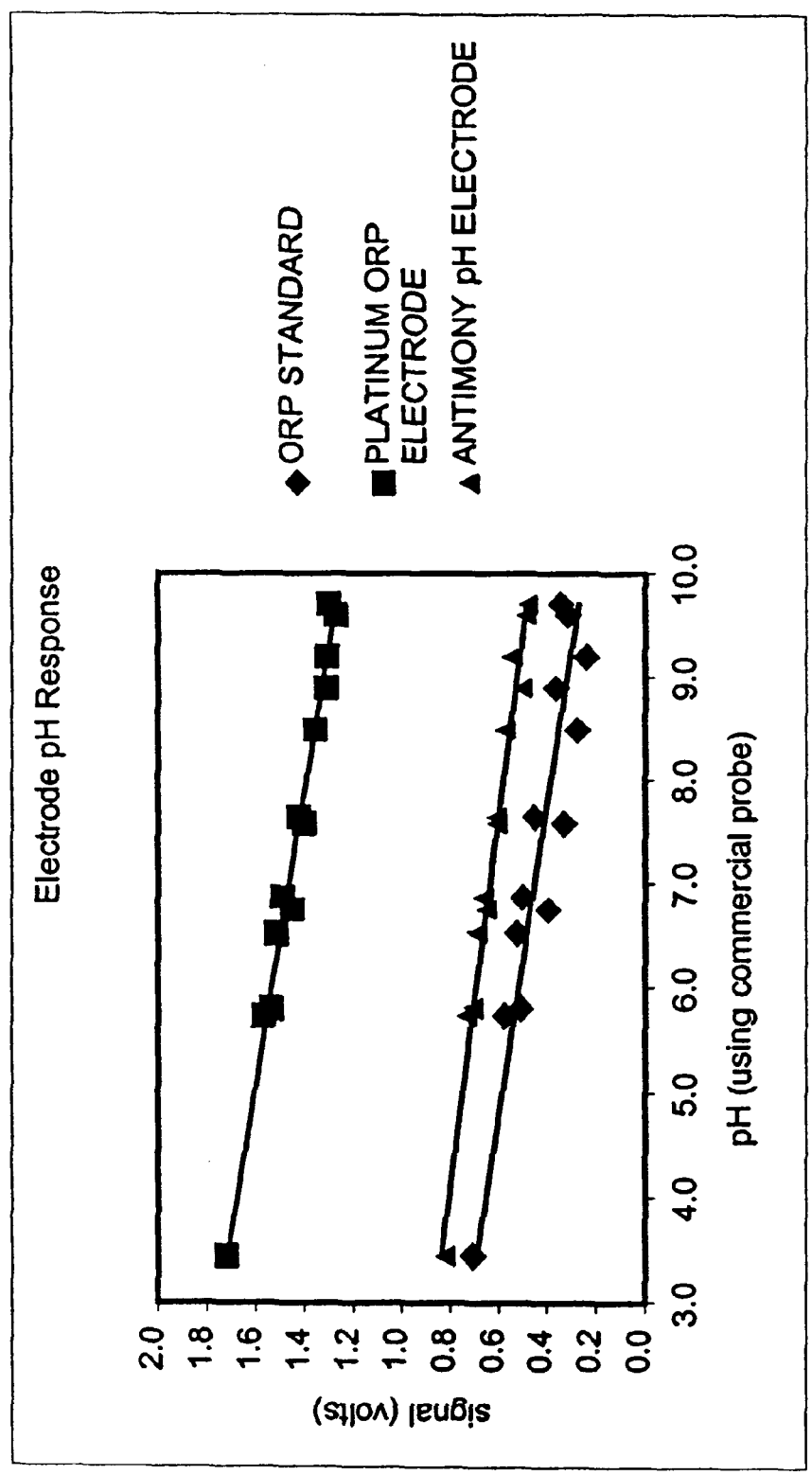
FIG. 9 is a graph of electrode pH response, with the pH as determined by a commercial pH probe as the ordinate (x coordinate) and the voltage between the test electrodes and reference electrode as the abscissa (y coordinate)
Figure 10:
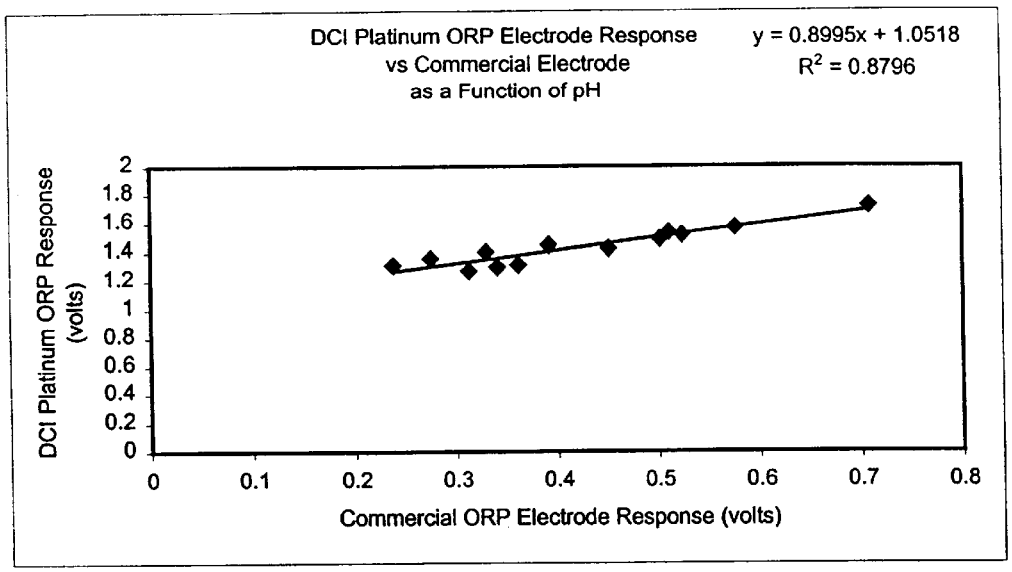
FIG. 10 is a graph of electrode ORP response, with the ORP as determined by a commercial pH probe and measured in volts as the ordinate (x coordinate) and the voltage between the test electrode and the reference electrode as the abscissa (y coordinate)
Figure 11:
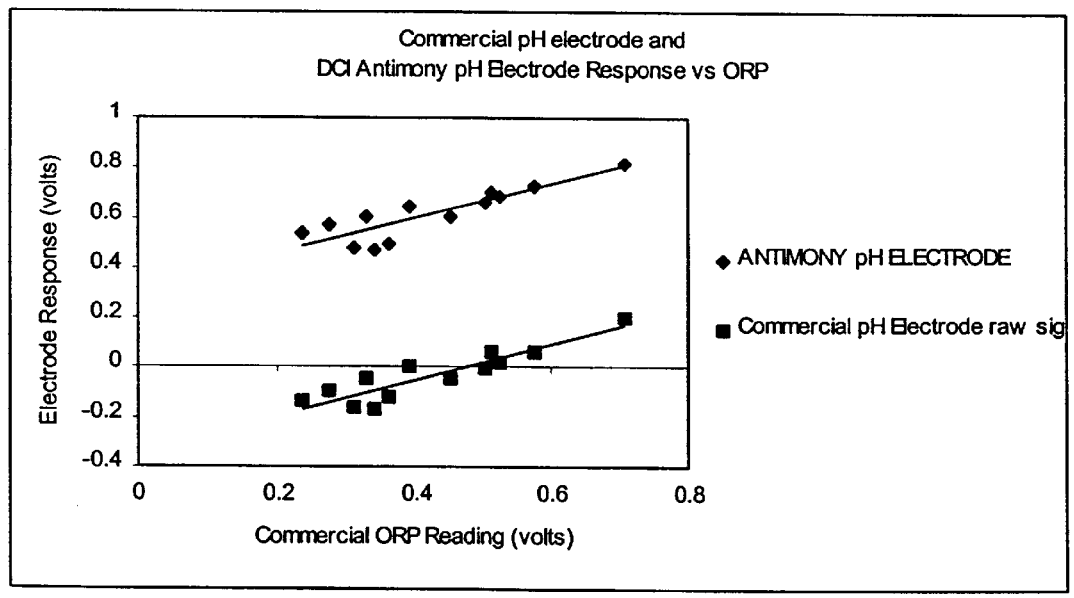
FIG. 11 is a graph of electrode pH versus ORP response, with the ORP as determined by a commercial ORP probe and measured in volts as the ordinate (x coordinate) and the voltage between the test electrodes and the reference electrode as the abscissa (y coordinate)

A beaker (250 ml) was filled with cold tap water and placed on a hot plate/stirrer. A magnetic stir bar was added into the beaker and a calibrated commercial pH, ORP and temperature sensor were inserted into the beaker along with antimony, platinum and 99.99% pure zinc electrodes of the present invention. The electrodes were suspended high enough in the beaker so as not to interfere with the magnetic stirrer. The pH, ORP and temperature of the water were measured and recorded with both the commercial and the electrodes of the present invention. The tap water tested typically has a pH of about 9.5, an ORP of about +200 mV and temperature of about 71° F. The initial pH was adjusted incrementally downward in several tests by addition of a proportional amount (about 5 mg) of an acidic chemical such as sodium bisulfate or muriatic Acid (referred to as pH-down chemical). After each addition of chemical the stirrer was run briefly at about 60 rpm until the solid chemical was dissolved. The pH is allowed to stabilize at various levels and the signal values of each sensor were recorded. In each of the tests, when the water pH was less than 5, the pH was adjusted incrementally upward by adding a proportional amount (about 5 mg) of an alkaline chemical such as soda ash or sodium bicarbonate (referred to as pH-up chemical). After each addition of chemical, the stirrer was run briefly at about 60 rpm until the solid chemical was dissolved. The pH was allowed to stabilize at various levels and the signal values of each sensor were recorded. The pH was adjusted upward until it reached about 9.5. The measured values of pH signals were then are plotted with the pH values indicated by the calibrated commercial probe on the horizontal (X) axis and the signal values from the commercial ORP electrode (identified as "ORP Standard"), the pH electrode of the present invention (identified as "Antimony pH Electrode"), and ORP electrode (identified as "Platinum ORP Electrode) on the vertical (Y) axis. This plot is shown in the graph of FIG. 9. This graph show that when very little oxidation or reduction is taking place (here, ORP is about 0.200V), both the commercial ORP electrode and the platinum ORP electrode of this invention exhibit a pH dependence. FIG. 10 shows the ORP signals plotted with the signals from the commercial ORP electrode (identified as "Commercial ORP Electrode Response") on the horizontal (X) axis and the signals from the ORP electrode of the present invention (identified as "DCI Platinum ORP Response") on the vertical (Y) axis. According to the graph of FIG. 10, the commercial ORP electrode shows a pH dependence similar to that of the ORP electrode of this invention. FIG. 11 shows the commercial ORP electrode response (identified as "Commercial ORP Reading") plotted on the horizontal (X) axis and the commercial pH electrode signal (identified as "Commercial pH Electrode raw sig") and the signal of the antimony pH electrode of the present invention (identified as "Antimony pH Electrode") plotted on the vertical (Y) axis. The graph of FIG. 11 shows that the commercial electrode exhibits an ORP dependence similar to that of the antimony pH electrode of the present invention.

EXAMPLE 2

Figure 12:
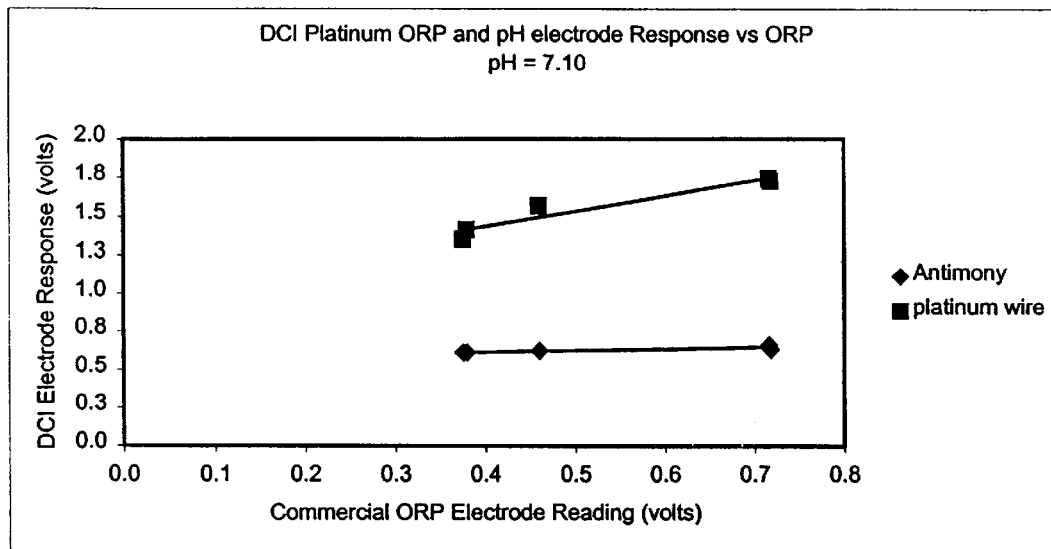
FIG. 12 is a graph of electrode pH response versus ORP response, with the ORP as determined by a commercial ORP probe and measured in volts as the ordinate (x coordinate) and the pH as measured by the voltage between the test electrode and the reference electrode as the abscissa (y coordinate)

A beaker (250 ml) was filled with cold tap water and placed on a hot plate/stirrer. A magnetic stir bar was added into the beaker and a calibrated commercial pH, ORP and temperature sensor were inserted into the beaker along with antimony, platinum and 99.99% pure zinc electrodes of the present invention. The electrodes were suspended high enough in the beaker so as not to interfere with the magnetic stirrer. The pH, ORP and temperature of the water were measured and recorded with both the commercial and the electrodes of the present invention. The tap water tested typically has a pH of about 9.5, an ORP of about +200 mV and temperature of about 71° F. This test was carried out after the pH exposure of Example 1, above, and the commercial ORP electrode took some time to return back to the original value that it had before the pH test. For each test, the initial pH was adjusted incrementally downward to about pH 7 by adding a proportional amount (about 2 mg) of an acidic chemical such as sodium bisulfate or muriatic Acid (pH-down). After each addition of chemical the stirrer was run briefly at about 60 rpm until the solid chemical dissolved. The pH was allowed to stabilize and then the signal values of each sensor were recorded. After the pH stabilized at around 7, a proportional amount (about 4 mg) of buffer salt (sodium hydrogen carbonate) was added to make the pH more stable. After each addition of chemical, the stirrer was run briefly at about 60 rpm until the solid chemical dissolved. At times, it was noted that the pH rose slightly after the buffer salt was added, and when that occurred, trace amounts of pH-down were added to bring the pH back to about 7. The amount of pH-down necessary to effect a decrease similar to that achieved in the first adjustment downward to pH 7 was higher than that required in the first adjustment downward higher since the solution had been buffered to resist small changes in the pH. When the pH was stable, a proportional amount of (about 2 mg) of a chlorinating compound (trichloro-s-triazinetrione) was added. The ORP was allowed to stabilize and the signal values of each sensor were recorded. After the initial reading from the previous step, the ORP was incrementally raised by adding trace amounts of chlorinating compound, letting the signal stabilize, and then recording the signal values. The amount of chlorinating compound required for this small beaker was extremely small and it is very easy to overdose. For the amount of chemical involved, the response time may be considerable. The signals were then plotted with the ORP values as indicated by the commercial probe on the horizontal (X) axis and the signal values from the pH and ORP sensors (identified as "Antimony" and "platinum wire", respectively) on the vertical (Y) axis. This plot is shown in the graph of FIG. 12. This graph shows that at a constant pH level, the antimony pH sensor was relatively independent of the ORP reading.

EXAMPLE 3

Figure 13:
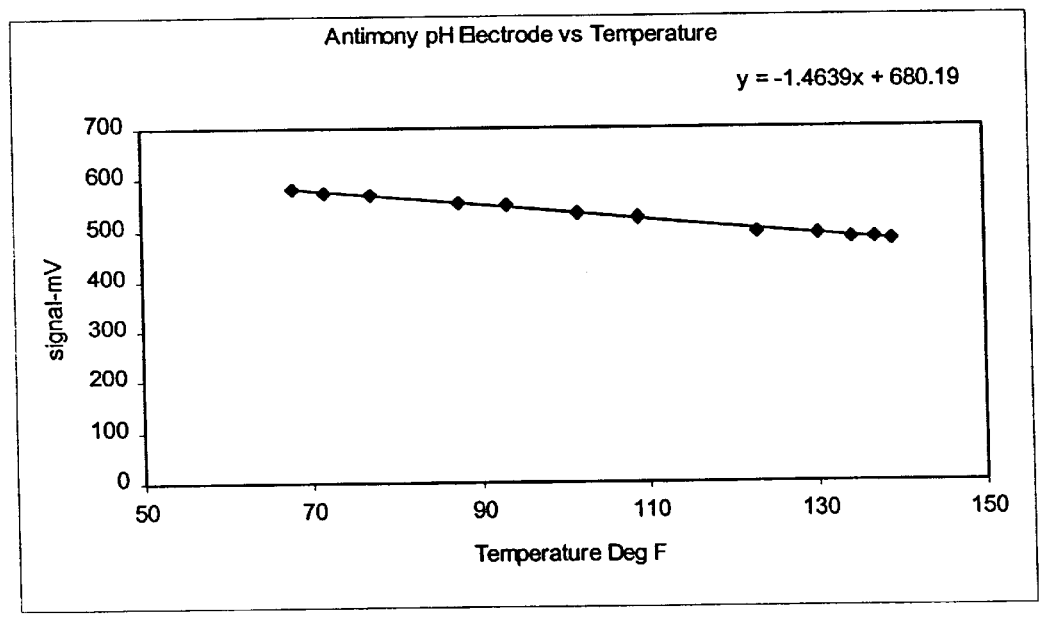
FIG. 13 is a graph of electrode pH response versus temperature, with the temperature as the ordinate (x coordinate) and the pH as measured by the voltage between the test electrode and the reference electrode as the abscissa (y coordinate)

A beaker (250 ml) was filled with cold tap water and placed on a hot plate/stirrer. A calibrated commercial pH, ORP and temperature sensor were inserted into the beaker along with a calibrated temperature probe and antimony, platinum and 99.99% pure zinc electrodes of the present invention. The electrodes were suspended high enough in the beaker so as not to touch the bottom of the beaker. The pH, ORP and temperature of the water were measured and recorded with both the commercial sensors and the electrodes of the present invention. The tap water tested typically has a pH of about 9.5, an ORP of about +200 mV and temperature of about 71° F. The Hot Plate was turned on to its lowest setting; i.e., #1. As the temperature rose, the signal on each sensor and the current temperature were recorded. The temperature then was plotted on the horizontal (X) axis and the signals from the other electrodes on the vertical (Y) axis. This plot is shown in the graph of FIG. 13 and illustrates that the temperature response of the antimony electrode is linear, with a slope of about −1.5 mV/° F.

EXAMPLE 4

Figure 14:
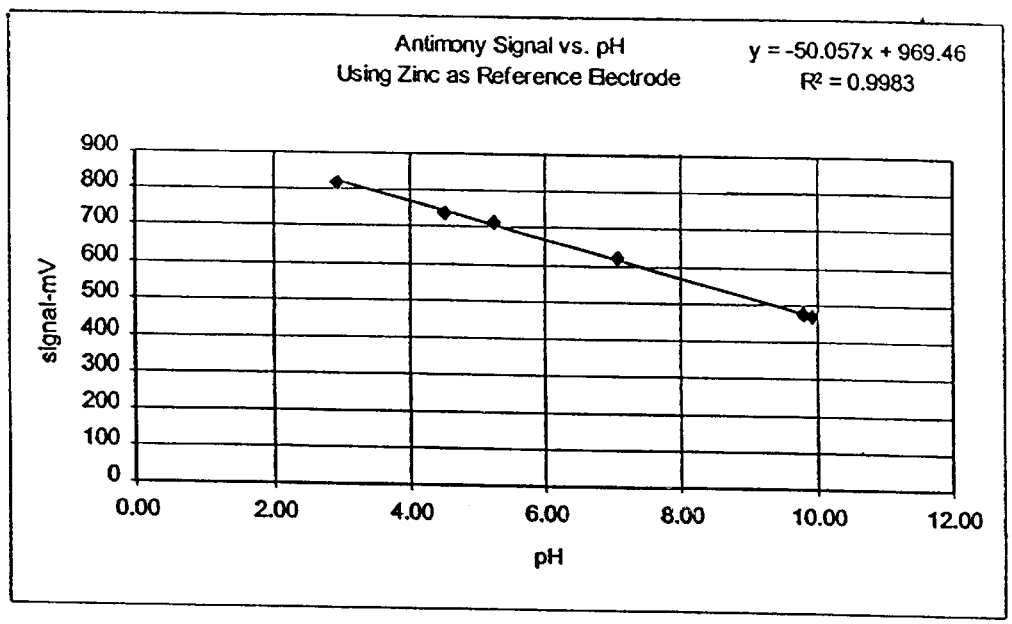
FIG. 14 is a graph of electrode pH response, with the pH as determined by a commercial pH probe as the ordinate (x coordinate) and the pH measured as the voltage between the test electrode and reference electrode as the abscissa (y coordinate)
Figure 15:
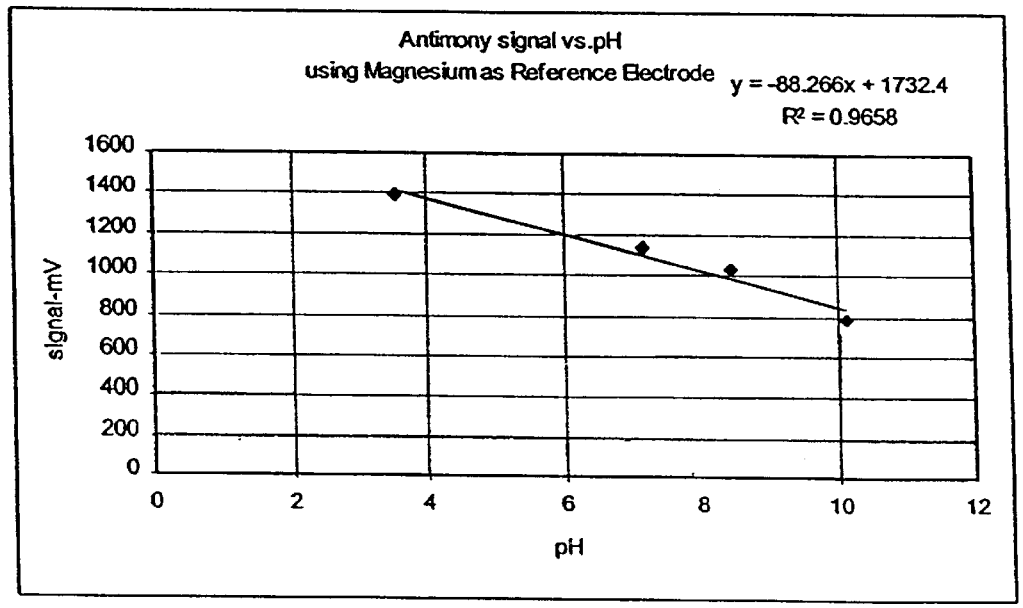
FIG. 15 is a graph of electrode pH response, with the pH as determined by a commercial pH probe as the ordinate (x coordinate) and the pH measured as the voltage between the test electrode and reference electrode as the abscissa (y coordinate).

By a method as described in Example 1, above, voltage readings were taken from the antimony electrode at various pH's as determined by the commercial pH sensor. The results were plotted on the graph shown in FIG. 14. The method was repeated with a magnesium reference electrode in place of the zinc electrode. The results were plotted on the graph shown in FIG. 15. It can be seen from FIGS. 14 and 15 that the voltage in both cases is linearly related to the pH.

In each case, $R^2$ has been calculated and shown to be very close to 1, establishing the relationship to linear to be extremely close. The formulae for the lines in each case have been determined, showing the relationship between the pH (x) and the voltage (y).

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

In view of the above, it will be seen that the several advantages of the invention are achieved and other advantageous results obtained. As various changes could be made in the above methods and compositions without departing from the scope of the invention, it is intended that all matter contained in the above description as shown in the accompanying drawings shall be interpreted as illustrative and not in a limiting sense.

What is claimed is:

1. A galvanic probe comprising
   a sensor electrode having an exposed surface comprising (1) a first material selected from the group consisting of noble metals, antimony, and bismuth, and (2) optionally, an oxide or hydroxide of the first material, and
   a reference electrode spaced apart from the sensor electrode and having an exposed surface comprising (1) a second material selected from the group consisting of zinc and magnesium, and (2) optionally, an oxide or hydroxide of the second material.

2. A galvanic probe as set forth in claim 1 wherein the first material is selected from the group consisting of antimony and bismuth.

3. A galvanic probe as set forth in claim 2 wherein the first material is antimony.

4. A galvanic probe as set forth in claim 3 wherein the sensor electrode is a first sensor electrode, and further comprising a second sensor electrode wherein the second sensor electrode has an exposed surface comprising a noble metal and, optionally, an oxide or hydroxide of the noble metal.

5. A galvanic probe as set forth in claim 4 wherein the noble metal is selected from the group consisting of platinum, silver and gold.

6. A galvanic probe as set forth in claim 5 wherein the noble metal is platinum.

7. A galvanic probe as set forth in claim 6 wherein the exposed surface of the reference electrode comprises zinc.

8. A galvanic probe as set forth in claim 7 wherein the exposed surface of the reference electrode consists essentially of zinc and, optionally, zinc oxide, zinc hydroxide or both.

9. A galvanic probe as set forth in claim 7 wherein the exposed surface of the reference electrode comprises zinc of purity in excess of 99.9% and, optionally, zinc oxide, zinc hydroxide or both.

10. A galvanic probe as set forth in claim 6, further comprising a first circuit, said first sensor electrode and said reference electrode generating a first signal when said first sensor electrode and said reference electrode are in contact with a fluid having a pH such that said first sensor electrode and said reference electrode are in electrochemical communication with each other, said first signal being input to and processed by said first circuit, and still further comprising a second circuit, said second sensor electrode and said reference electrode generating a signal when said second sensor electrode and said reference electrode are in contact with a fluid having an ORP such that said second sensor electrode and said reference electrode are in electrochemical communication with each other, said second signal being input to and processed by said second circuit.

11. A galvanic probe as set forth in claim 10 wherein a voltage differential exists between each sensor electrode and the reference electrode and the signals are the voltage differentials or amperages of currents flowing through the respective circuits, said currents being produced galvanically by the electrodes in interaction with the fluid.

12. A galvanic probe as set forth in claim 11 wherein said first circuit comprises a first signal processor, said second signal processor translating the first signal to information indicative of the pH of the fluid, and said second circuit comprises a second signal processor, said second signal processor translating the signal to information indicative of the ORP of the fluid.

13. A galvanic probe as set forth in claim 12 wherein the first signal processor transmits the information to a display that displays the pH of the fluid, and the second signal processor transmits the information to a display that displays the ORP of the fluid.

14. A galvanic probe as set forth in claim 13 wherein the display for displaying the pH levels is a first display and the display for displaying the ORP levels is a second display, the first display is in wireless communication with the first signal processor and the second display is in wireless communication with the second signal processor.

15. A method for measuring the oxidation reduction potential of a fluid, comprising placing the electrodes of the galvanic probe of claim 13 into a fluid and reading the oxidation reduction potential from the display.

16. A galvanic probe as set forth in claim 11 wherein said first circuit comprises a first signal processor, the first signal processor translating the first signal to pH-related information indicative of an amount of a composition that should to be added to the fluid to adjust the pH of the fluid to a desired pH, and said second circuit comprises a second signal processor, the second signal processor translating the second signal to ORP-related information indicative of an amount of a composition that should to be added to the fluid to adjust the ORP of the fluid to a desired ORP.

17. A galvanic probe as set forth in claim 16 wherein the first signal processor transmits the pH-related information to a display for displaying data from which may be determined the amount of a composition that should to be added to the fluid to adjust the pH of the fluid to the desired pH, and the second signal processor transmits the ORP-related information to a display for displaying data from which may be determined the amount of a composition that should to be added to the fluid to adjust the ORP of the fluid to the desired ORP.

18. A galvanic probe as set forth in claim 3 wherein the exposed surface of the reference electrode comprises zinc.

19. A galvanic probe as set forth in claim 18 wherein the exposed surface of the reference electrode consists essentially of zinc and, optionally, zinc oxide, zinc hydroxide or both.

20. A galvanic probe as set forth in claim 18 wherein the exposed surface of the reference electrode comprises zinc of purity in excess of 99.9% and, optionally, zinc oxide, zinc hydroxide or both.

21. A galvanic probe as set forth in claim 18, further comprising a circuit, said electrodes generating a signal when the electrodes are in contact with a fluid having a pH such that the electrodes are in electrochemical communication with each other, the signal being input to and processed by said circuit.

22. A galvanic probe as set forth in claim 21 wherein a voltage differential exists between the electrodes and the signal is the voltage differential or amperage of a current flowing through the circuit, said current being produced galvanically by the electrodes in interaction with the fluid.

23. A galvanic probe as set forth in claim 22 wherein said circuit comprises a signal processor and the signal processor translates the signal to information indicative of the pH of the fluid.

24. A galvanic probe as set forth in claim 23 wherein the signal processor transmits the information to a display that displays the pH of the fluid.

25. A galvanic probe as set forth in claim 24 wherein the display is in wireless communication with the signal processor.

26. A method for measuring pH of a fluid, comprising placing the electrodes of the galvanic probe of claim 24 into a fluid and reading the pH from the display.

27. A galvanic probe as set forth in claim 22 wherein said circuit comprises a signal processor and the signal processor translates the signal to information indicative of an amount of a composition that should to be added to the fluid to adjust the pH of the fluid to a desired pH.

28. A galvanic probe as set forth in claim 22 wherein the signal processor transmits the information to a display for displaying data from which may be determined the amount of a composition that should to be added to the fluid to adjust the pH of the fluid to the desired pH.

29. A galvanic probe as set forth in claim 2, further comprising a second sensor electrode wherein the second sensor electrode has an exposed surface comprising a noble metal and, optionally, an oxide or hydroxide of the noble metal.

30. A galvanic probe as set forth in claim 29 wherein the noble metal is selected from the group consisting of platinum, silver and gold.

31. A galvanic probe as set forth in claim 30 wherein the noble metal is platinum.

32. A galvanic probe as set forth in claim 2, further comprising a circuit, said electrodes generating a signal when the electrodes are in contact with a fluid having a pH such that the electrodes are in electrochemical communication with each other, the signal being input to and processed by said circuit.

33. A galvanic probe as set forth in claim 32 wherein a voltage differential exists between the electrodes and the signal is the voltage differential or amperage of a current flowing through the circuit, said current being produced galvanically by the electrodes in interaction with the fluid.

34. A galvanic probe as set forth in claim 33 wherein said circuit comprises a signal processor and the signal processor translates the signal to information indicative of the pH of the fluid.

35. A galvanic probe as set forth in claim 34 wherein the signal processor transmits the information to a display that displays the pH of the fluid.

36. A galvanic probe as set forth in claim 35 wherein the display is in wireless communication with the signal processor.

37. A method for measuring pH of a fluid, comprising placing the electrodes of the galvanic probe of claim 35 into a fluid and reading the pH from the display.

38. A galvanic probe as set forth in claim 33 wherein said circuit comprises a signal processor and the signal processor translates the signal to information indicative of an amount of a composition that should to be added to the fluid to adjust the pH of the fluid to a desired pH.

39. A galvanic probe as set forth in claim 38 wherein the signal processor transmits the information to a display for displaying data from which may be determined the amount of a composition that should to be added to the fluid to adjust the pH of the fluid to the desired pH.

40. A galvanic probe as set forth in claim 1 wherein the first material is a noble metal.

41. A galvanic probe as set forth in claim 40 wherein the first material is selected from the group consisting of platinum, silver and gold.

42. A galvanic probe as set forth in claim 41 wherein the first material is platinum.

43. A galvanic probe as set forth in claim 42 wherein the exposed surface of the reference electrode comprises zinc.

44. A galvanic probe as set forth in claim 43 wherein the exposed surface of the reference electrode consists essentially of zinc and, optionally, zinc oxide, zinc hydroxide or both.

45. A galvanic probe as set forth in claim 43 wherein the exposed surface of the reference electrode comprises zinc of purity in excess of 99.9% and, optionally, zinc oxide, zinc hydroxide or both.

46. A galvanic probe as set forth in claim 42, further comprising a circuit, said electrodes generating a signal when the electrodes are in contact with a fluid having an ORP such that the electrodes are in electrochemical communication with each other, the signal being input to and processed by said circuit.

47. A galvanic probe as set forth in claim 46 wherein a voltage differential exists between the electrodes and the signal is the voltage differential or amperage of a current flowing through the circuit, said current being produced galvanically by the electrodes in interaction with the fluid.

48. A galvanic probe as set forth in claim 47 wherein said circuit comprises a signal processor and the signal processor translates the signal to information indicative of the ORP of the fluid.

49. A galvanic probe as set forth in claim 48 wherein the signal processor transmits the information to a display that displays the ORP of the fluid.

50. A galvanic probe as set forth in claim 49 wherein the display is in wireless communication with the signal processor.

51. A galvanic probe as set forth in claim 49 wherein the oxidation reduction potential measurements correspond to chlorine levels in the fluid.

52. A method for measuring the oxidation reduction potential of a fluid, comprising placing the electrodes of the galvanic probe of claim 49 into a fluid and reading the oxidation reduction potential from the display.

53. A galvanic probe as set forth in claim 47 wherein said circuit comprises a signal processor and the signal processor translates the signal to information indicative of an amount of a composition that should to be added to the fluid to adjust the ORP of the fluid to a desired ORP.

54. A galvanic probe as set forth in claim 47 wherein the signal processor transmits the information to a display for displaying data from which may be determined the amount of a composition that should to be added to the fluid to adjust the ORP of the fluid to the desired ORP.

55. A galvanic probe as set forth in claim 1 wherein the exposed surface of the reference electrode comprises zinc.

56. A galvanic probe as set forth in claim 55 wherein the exposed surface of the reference electrode consists essentially of zinc and, optionally, zinc oxide, zinc hydroxide or both.

57. A galvanic probe as set forth in claim 55 wherein the exposed surface of the reference electrode comprises zinc of purity in excess of 99.9% and, optionally, zinc oxide, zinc hydroxide or both.

58. A method comprising contacting an aqueous liquid with the galvanic probe of claim 1.

59. A method as set forth in claim 58 wherein the galvanic probe further comprises a circuit, the aqueous liquid has a pH, and the electrodes of the galvanic probe generate a signal when the electrodes are in contact with the aqueous liquid such that the electrodes are in electrochemical communication with each other, the signal being input to and processed by said circuit.

60. A device for controlling the pH of a fluid in a vessel to a desired pH level, comprising:
    (a) a sensor electrode having an exposed surface comprising (1) a first material selected from the group consisting of antimony, and bismuth, and (2) optionally, an oxide or hydroxide of the first material;
    (b) a reference electrode spaced apart from the sensor electrode and having an exposed surface comprising (1) a second material selected from the group consisting of zinc and magnesium, and (2) optionally, an oxide or hydroxide of the second material; and
    (c) a circuit;
arranged such that said electrodes generate a signal when the electrodes are in contact with a fluid having a pH such that the electrodes are in electrochemical communication with each other, the signal being input to and processed by said circuit.

61. A device as set forth in claim 60, further comprising a signal processor, the signal processor translating the signal to information indicative of an amount of a composition that should to be added to the fluid to adjust the pH of the fluid to a desired pH.

62. A device as set forth in claim 61, further comprising a supply of the composition and a dispenser control in communication with the signal processor such as to receive the information, the dispenser control causing the amount of the composition that should to be added to the fluid to be dispensed in response to receipt of the information.

63. A device for controlling the pH of a fluid in a vessel to a desired ORP level, comprising:
    (a) a sensor electrode having an exposed surface comprising (1) a noble metal, and (2) optionally, an oxide or hydroxide of the noble metal;
    (b) a reference electrode spaced apart from the sensor electrode and having an exposed surface comprising (1) a material selected from the group consisting of zinc and magnesium, and (2) optionally, an oxide or hydroxide of the material; and
    (c) a circuit;
arranged such that said electrodes generate a signal when the electrodes are in contact with a fluid having an ORP such that the electrodes are in electrochemical communication with each other, the signal being input to an processed by said circuit.

64. A device as set forth in claim 63, further comprising a signal processor, the signal processor translating the signal to information indicative of an amount of a composition that should to be added to the fluid to adjust the ORP of the fluid to a desired ORP.

65. A device as set forth in claim 64, further comprising a supply of the composition and a dispenser control in communication with the signal processor such as to receive the information, the dispenser control causing the amount of the composition that should to be added to the fluid to be dispensed in response to receipt of the information.

66. A device as set forth in claim 65 wherein the oxidation reduction potentials correspond to chlorine levels in the fluid.

67. A galvanic cell comprising an electrolyte in contact with:
    a) a sensor electrode having an exposed surface comprising (1) a first material selected from the group consisting of noble metals, antimony, and bismuth, and (2) optionally, an oxide or hydroxide of the first material; and
    b) a reference electrode spaced apart from the sensor electrode and having an exposed surface comprising (1) a second material selected from the group consisting of zinc and magnesium, and (2) optionally, an oxide or hydroxide of the second material.

68. A galvanic cell as set forth in claim 67, wherein the first material is selected from the group consisting of antimony and bismuth.

69. A galvanic cell as set forth in claim 68 wherein the first material is antimony.

70. A galvanic probe as set forth in claim 69 wherein the exposed surface of the reference electrode comprises zinc.

71. A galvanic probe as set forth in claim 70 wherein the exposed surface of the reference electrode consists essentially of zinc and, optionally, zinc oxide, zinc hydroxide or both.

72. A galvanic probe as set forth in claim 70 wherein the exposed surface of the reference electrode comprises zinc of purity in excess of 99.9% and, optionally, zinc oxide, zinc hydroxide or both.

73. A galvanic probe as set forth in claim 68 wherein the exposed surface of the reference electrode comprises zinc.

74. A galvanic probe as set forth in claim 73 wherein the exposed surface of the reference electrode consists essentially of zinc and, optionally, zinc oxide, zinc hydroxide or both.

75. A galvanic probe as set forth in claim 73 wherein the exposed surface of the reference electrode comprises zinc of purity in excess of 99.9% and, optionally, zinc oxide, zinc hydroxide or both.

76. A galvanic cell as set forth in claim 67 wherein the first material is a noble metal.

77. A galvanic cell as set forth in claim 76 wherein the first material is platinum.

78. A galvanic probe as set forth in claim 77 wherein the exposed surface of the reference electrode comprises zinc.

79. A galvanic probe as set forth in claim 78 wherein the exposed surface of the reference electrode consists essentially of zinc and, optionally, zinc oxide, zinc hydroxide or both.

80. A galvanic probe as set forth in claim 78 wherein the exposed surface of the reference electrode comprises zinc of purity in excess of 99.9% and, optionally, zinc oxide, zinc hydroxide or both.

81. A galvanic probe as set forth in claim 76 wherein the exposed surface of the reference electrode comprises zinc.

82. A galvanic probe as set forth in claim 81 wherein the exposed surface of the reference electrode consists essentially of zinc and, optionally, zinc oxide, zinc hydroxide or both.

83. A galvanic probe as set forth in claim 81 wherein the exposed surface of the reference electrode comprises zinc of purity in excess of 99.9% and, optionally, zinc oxide, zinc hydroxide or both.

* * * * *

UNITED STATES PATENT AND TRADEMARK OFFICE
CERTIFICATE OF CORRECTION

PATENT NO.     : 6,653,842 B2
DATED          : November 25, 2003
INVENTOR(S)    : Mosely, Michael David, Decker, Paul, Martzall, Thomas Lee It is certified that error appears in the above-identified patent and that said Letters Patent is hereby corrected as shown below:

<u>Column 22,</u>
Claims 70-81, should read as follows:

70. A galvanic [[probe]] <u>cell</u> as set forth in claim 66 wherein the exposed surface of the reference electrode comprises zinc.

71. A galvanic [[probe]] <u>cell</u> as set forth in claim 70 wherein the exposed surface of the reference electrode consists essentially of zinc and, optionally, zinc oxide, zinc hydroxide or both.

72. A galvanic [[probe]] <u>cell</u> as set forth in claim 70 wherein the exposed surface of the reference electrode comprises zinc of purity in excess of 99.9% and, optionally, zinc oxide, zinc hydroxide or both.

73. A galvanic [[probe]] <u>cell</u> as set forth in claim 67 wherein the exposed surface of the reference electrode comprises zinc.

74. A galvanic [[probe]] <u>cell</u> as set forth in claim 73 wherein the exposed surface of the reference electrode consists essentially of zinc and, optionally, zinc oxide, zinc hydroxide or both.

75. A galvanic [[probe]] <u>cell</u> as set forth in claim 73 wherein the exposed surface of the reference electrode comprises zinc of purity in excess of 99.9% and, optionally, zinc oxide, zinc hydroxide or both.

76. A galvanic [[probe]] <u>cell</u> as set forth in claim 68 wherein the exposed surface of the reference electrode comprises zinc.

77. A galvanic [[probe]] <u>cell</u> as set forth in claim 76 wherein the exposed surface of the reference electrode consists essentially of zinc and, optionally, zinc oxide, zinc hydroxide or both.

78. A galvanic [[probe]] <u>cell</u> as set forth in claim 76 wherein the exposed surface of the reference electrode comprises zinc of purity in excess of 99.9% and, optionally, zinc oxide, zinc hydroxide or both.

79. A galvanic [[probe]] <u>cell</u> as set forth in claim 69 wherein the exposed surface of the reference electrode comprises zinc.

80. A galvanic [[probe]] <u>cell</u> as set forth in claim 79 wherein the exposed surface of the reference electrode consists essentially of zinc and, optionally, zinc oxide, zinc hydroxide or both.

81. A galvanic [[probe]] <u>cell</u> as set forth in claim 79 wherein the exposed surface of the reference electrode comprises zinc of purity in excess of 99.9% and, optionally, zinc oxide, zinc hydroxide or both.

Signed and Sealed this

Twenty-third Day of March, 2004

JON W. DUDAS
*Acting Director of the United States Patent and Trademark Office*